United States Patent [19]

Bellina

[11] Patent Number: 4,604,998
[45] Date of Patent: Aug. 12, 1986

[54] LASER SURGERY DRAPE

[76] Inventor: Joseph H. Bellina, 3439 Kabel Dr., New Orleans, La. 70114

[21] Appl. No.: 598,994

[22] Filed: Apr. 11, 1984

[51] Int. Cl.$^4$ ............................................. A61F 13/00
[52] U.S. Cl. ............................. 128/132 D; 250/516.1
[58] Field of Search ............... 128/132 D, 202.23, 362, 128/395, 398, 303.1; 250/515.1, 516.1, 519.1; 350/1.7; 5/502, 483, 459, 482, 500

[56] References Cited

U.S. PATENT DOCUMENTS

| | | |
|---|---|---|
| 1,611,031 | 12/1926 | Henderson . |
| 2,479,094 | 8/1949 | Bicknell . |
| 2,683,262 | 7/1954 | Foss . |
| 3,035,956 | 5/1962 | Gonda et al. . |
| 3,059,364 | 10/1962 | Landsberg et al. . |
| 3,098,780 | 7/1963 | Krause . |
| 3,132,344 | 5/1964 | Langdon ................... 2/81 |
| 3,164,840 | 1/1965 | Reynolds ................... 2/81 |
| 3,251,360 | 5/1966 | Melges . |
| 3,394,260 | 7/1968 | Phipps ............................ 250/516.1 |
| 3,542,019 | 11/1970 | Gittins . |
| 3,720,836 | 3/1973 | Douges et al. ................ 250/519.1 |
| 3,871,739 | 3/1975 | Poulsen ........................... 350/1.7 |
| 3,878,843 | 4/1975 | Morgan . |
| 4,021,362 | 5/1977 | Glasser et al. . |
| 4,041,942 | 8/1977 | Dougan et al. . |
| 4,196,355 | 4/1980 | Maine . |
| 4,378,794 | 4/1983 | Collins . |

*Primary Examiner*—Gene Mancene
*Assistant Examiner*—John G. Weiss
*Attorney, Agent, or Firm*—Pravel, Gambrell, Hewitt & Kimball

[57] ABSTRACT

A layered drape apparatus useful during laser surgery protects the patient from inadvertent laser radiation damage by diffusing radiation which leaves the operative field. The apparatus includes metallic and non-metallic layers with an airspace therebetween.

18 Claims, 5 Drawing Figures

LASER SURGERY DRAPE

BACKGROUND OF THE INVENTION

1. Technical Field

The present invention relates to surgical drapes, and more particularly relates to a multi-layered drape for protecting patients during laser surgery.

2. Background Art

Many new surgical techniques have been developed for the treatment of cancer among other things. Laser surgery requires the use of a laser beam which can be harmful to the patient if it is misdirected or misapplied for a long period of time. It would therefore be desirable to have a drape which would maintain a sterile area about the operation and at the same time provide protection to the patient from the laser beam for areas outside the operative area.

Various devices have been patented which use one or more layers of material for protecting individuals from radiation. A discussion of various such patented devices follows hereinafter.

U.S. Pat. No. 1,611,031 entitled "Compound Fabric" issued to T. Henderson in 1926. This invention relates to a compound material of that kind which comprises layers of lead or other metal foil and a flexible material for protecting same. The material consists of a layer of thin thread fabric preferably previously waterproofed overlying at one or both sides a layer of lead or other metal foil which is supported by thin paper on one or both sides, said paper being preferably attached to the foil by waterproof adhesive.

U.S. Pat. No. 2,479,094 issued in 1949 to J. A. Bickness and is entitled "Dual-Toned Metallic-Coated Web." The process of making the dual-toned metallic-coated flexible webs comprises applying a metallic-coating to a suitable flexible base by any desired or conventional means: the so-coated web is then acted upon, by mechanical means, at divers spots or areas whereby the areas acted upon are changed in respect to brilliance, gloss, metallic appearance or the like from their original condition and from other areas of the sheet which are unacted upon or acted upon to a lesser degree.

U.S. Pat. No. 2,683,262 entitled "Protective Cover" issued July 13, 1953 to B. Foss. The invention basically discloses a covering member preferably made of white cloth, such as cotton or muslin, comprising a front portion, and a back portion of generally rectangular configuration, capable of at least partially reflecting the rays caused by an atomic bomb explosion.

U.S. Pat. No. 3,098,780 issued to J. N. Krause issued July 23, 1963 relates particularly to a curl resistant metallic foil to paper lamination and processes for producing such laminations.

U.S. Pat. No. 3,251,360 entitled "Gynecology or Lithotomy Drape" issued May 17, 1966 to F. J. Melges. This invention discloses an improved gynecology or lithotomy drape of unitary form which has no separate legging to attach to same, and which is adapted to fully cover a patient conventionally resting on an operating or delivery table with the patient's legs and feet supported in elevated position by means of stirrups.

U.S. Pat. No. 3,035,956 issued May 22, 1962 to D. Gonda et al and is entitled "Flexible Protective Covering Sheet Material." This patent discloses protective covering materials for packaging and preserving an item liable to corrosion or other deterioration under the action of moisture or moisture vapour comprising a tough pre-fabricated flexible material which is completely proof against moisture and moisture vapour even after being repeatedly folded or crumpled and is capable of being easily joined to another part of the same material in a moisture and moisture proof manner, for example, by heat sealing.

U.S. Pat. No. 3,059,364 issued in 1962 shows a flexible protective covering sheet material comprising a layer of lead foil and a sheet of fabric reinforced flexible corrosion resistant heat-sealable material having a thickness of not less than 0.01 inch adhered to each side of the said foil.

U.S. Pat. No. 3,542,019 entitled "Catheter Drape and Wrap issued in Ramona Gittins in 1970 pertains to a medical drape, adapted to provide a sterile field for performing a catheterization procedure and other medical and surgical procedures. Another feature covered herein is a novel method of performing the catheterization procedure using the new drape. As a secondary feature, the drape also serves as a wrapping for storing the medical and surgical equipment in a sterile field prior to performance of the procedure. The drape, adapted to be draped over the patient, comprises a sterilizable, foldable sheet of material having an opening formed therein through which the procedure is performed and having graspable means disposed thereon for unfolding the material without contaminating the sterile field.

U.S. Pat. No. 3,878,843 issued in 1975 to B. Morgan shows a surgical drape or laminate including a plastic film with a layer of pressure sensitive adhesive on one face surface of the film and a flexible paper conter cover layer thereover, and parallel pairs of cover strip means on edge portions of the adhesive whereby when an inner cover strip is removed, the edges of the laminate can be folded inwardly on themselves to provide a thickened laminate for drape grip and handling action.

U.S. Pat. No. 4,041,942 issued on Aug. 16, 1977 and discloses a drape for use in surgical procedures including a sterile sheet, a generally diamond-shaped opening in the sheet, and a slot extending from a corner of the opening to an edge of the sheet. The sheet is constructed of a disposable non-woven cellulosic material and the opening and the slot have folded edges formed by reversely folded portions of the material. A reinforcing sheet having a matching diamond-shaped opening and a matching slot can be secured to the main sheet in superimposed relation. The main sheet and the reinforcing sheet have respective openings and slots in direct alignment to define a fenestrated surgical drape having a pair of split end portions.

U.S. Pat. No. 4,021,862 issued on May 10, 1977 to Herman Glasser et al and shows a radiation eye shield adapted to protect the wearer from the hazards of direct beam and scattered radiation. In one embodiment, the entire eye shield is of a high density material and in another example of the invention, the shield comprises goggles having a pair of lead-glass lenses and lead impregnated vinyl shielding applied to the front and side surfaces of the goggles surrounding the lenses.

U.S. Pat. No. 4,196,355 entitled "Radiation Shield Vest and Skirt" issued in 1980 to Gayle Maine shows a two-piece radiation shield garment for the human body comprising an adjustably overlapping vest to protect the upper body and a wraparound skirt to protect the lower body. The vest and skirt are constructed of multiple inner layers of flexible radiation shielding material covered with nonshielding fabric or other material. The vest and skirt may be attractively fashioned and decorated to encourage their use as a shield garment for women. The vest includes a rear shield panel joined to a pair of overlapping front shield panels.

U.S. Pat. No. 4,378,794 entitled "Surgical Drape" issued to Robert F. Collins on Apr. 5, 1983 discloses a surgical drape comprising, a main sheet of flexible material having a fenestration, and an opening in the expected path of fluid runoff from the fenestration. The drape has a fluid pervious screen covering the opening. The drape also has a pocket comprising a flap covering a lower portion of the screen, with the flap having an upper edge and defining a cavity facing toward the expected path of fluid runoff from the fenestration.

None of the prior art devices above-discussed provides a surgical drape suitable for protection of a patient from laser beams during a laser surgical operation.

GENERAL DISCUSSION OF THE PRESENT INVENTION

The present invention solves the prior art problems and shortcomings by providing a laser surgery drape which comprises a multi-layered drape having at least one or more metallic layers which are adhered to at least one non-metallic fabric layer. A reflective surface is formed between the two layers for diffusing a laser ray which penetrates one of the layers. In the preferred embodiment, the multi-layered drape includes a first non-metallic layer of cloth, paper, or other such fabric. A second metallic layer is fastened to the non-metallic layer so that each layer provides an inner surface which faces the inner surface of the other. A flexible metallic surface is adhered to the inner surface of the non-metallic layer.

In the preferred embodiment, the layers are only peripherally joined so that an air space is formed between the two layers, each layer having a reflective surface which communicates with the air space.

In the preferred embodiment the reflective surfaces are flexible, metallic surfaces. The metallic surfaces, are preferably polished, mirrored surfaces.

The non-metallic layer can be a fabric such as cloth. Alternatively, the non-metallic layer can be a disposable, fabric-like material such as paper. The metallic layer can be a suitable polished metallic material such as aluminum, for example.

The laser drape design is composed of materials that will allow for absorption of all wave lengths from the ultraviolet through the visible into the infrared wave lengths.

The drape material is constructed such that the outer layer and the black undercoating layer acts as a thermal absorption layer creating a microplasma at the surface of the aluminum thin foil. The aluminum foil has a thickness of, for example, 0.01 milimeters. This microplasma's thermal effect is to vaporize the outer layer of aluminum, and penetration through the outer shell occur. Once the penetration has been completed, the inner aluminum layer which is completely reflective noncoated begins to bounce internally the laser wave lengths and dissipates through inner heat dissipation by internal reflection along the inner surfaces. Currently available lasers such as the carbon dioxide laser, Argon laser, Nd:YAG lasers, all in the focused mode would or potentially could create a microplasma causing outer penetration and entrapment within the folds of the laser drape as above designed.

This drape will encompass all wave lengths that would create a plasma or thermal effect on the outer layers creating a penetration and entrapping of the beam regardless of wave length. Examples of the current wavelengths of lasers are the carbon dioxide laser with a wavelength of, eg., 10.6 microns, and the Nd:YAG laser with a wavelength of, eg., 1.06 microns, and the Argon laser with visible wave lengths between 400 to 500 mm.

The single upper layer of the laser drape can act as a complete thermal barrier for the patient. The design of the drape is such that the outer cloth layer is comprised of soft material (does not have any specific purpose) which acts as a resting pad. The inner aspect is black. The black color is an absorber of heat so any radiation in the room will be absorbed by the black layer and transferred to the inner silvered (aluminum) layer and acts as a radiator to the patient. In addition, when the patient is laying on the table, the patient's body heat will transfer to the metallic, silvered surface and reflect back down to the patient. As a result a thermos bottle effect is created around the patient. This creates an isotherm drape, i.e., equally heated.

In addition to draping material, the edge of the drape can be equipped with a small ground wire with an alligator clip which when clipped to a ground wire protects the patient from electrical burns. If the surgeon happens to drop an electrical surgical unit and hit the foot switch, normally the doctor, patient or technician can be burned. With the present invention, the electricity is dissipated through grounding when the electrical surgical instrument hits the drape. The patient is isolated. If the surgeon is using an electrical surgical unit and the unit is accidentally activated while resting on the patient, the patient will not be burned because the entire system is grounded out. Current will be carried away from the patient because the drape is more conductive than the patient body that is covered.

The present invention can be used with conventional medical lasers such as the NIIC 50 YD laser with a maximum tube output of 52 watts at tissue level with a focusing lens creating a 100 micron beam (exemplary). The drape of the present invention has been successfully used with the following lasers: (1) Cooper laser under the marketing name of NIIC laser, (2) Sharplan Laser (all models) (3) Cavitron laser, and (4) Coherent laser including Merrimack laser.

BRIEF DESCRIPTION OF THE DRAWINGS

For a further understanding of the nature and objects of the present invention, reference should be had to the following detailed description, taken in conjunction with the accompanying drawings, in which like parts are given like reference numerals and wherein.

DETAILED DESCRIPTION OF THE PRESENT INVENTION

Figure 1:
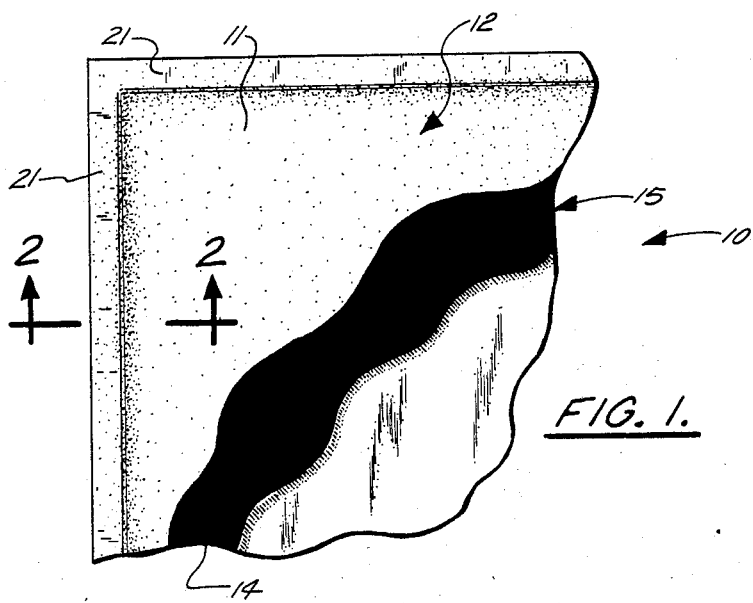
FIG. 1 is a fragmentary, top view of the preferred embodiment of the apparatus of the present invention.

In FIG. 1, laser surgery drape 10 can be seen as comprising an upper, non-metallic layer 11, having an upper surface 12 to which is bonded using cement layer 13, and a first upper metallic layer 14. The uppermost surface 15 of metallic layer 14 is blackened, while the lower surface 16 thereof is highly polished and/or mirrored. A bottom layer 17 is preferably a metallic layer having an inside surface 18 which is highly polished and an under surface 19 which likewise is preferably highly polished.

Figure 2:
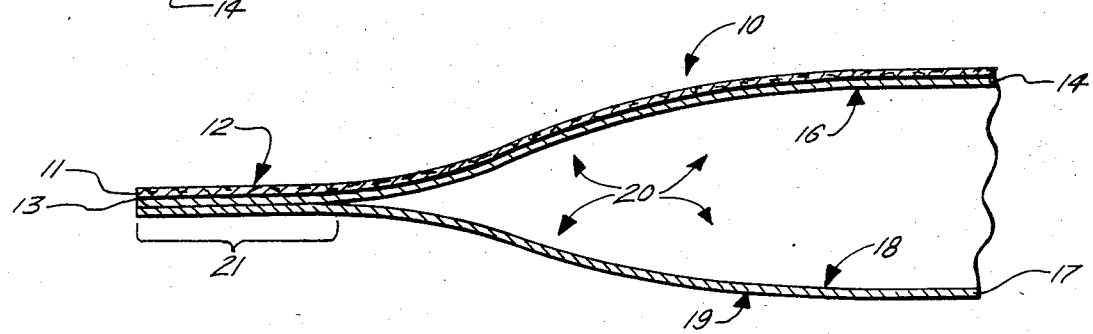
FIG. 2 is a partial, sectional view of the preferred embodiment of the apparatus of the present invention taken along lines 2—2 of FIG. 1.

An air space 20 is maintained between the uppermost metallic layer 14 and the lowermost metallic layer 17. The drape 10 is preferably peripherally joined at peripheral edge 21, as is illustrated in FIGS. 1 and 2 of the drawings. Thus, for example, drape 10 could be rectangular, or square, or circular with its periphery providing a continuous bonded edge 21 as shown in FIGS. 1 and 2. The layers 11, 14 and 17 could be peripherally bound using cement, stitching, or the like.

Figure 4:
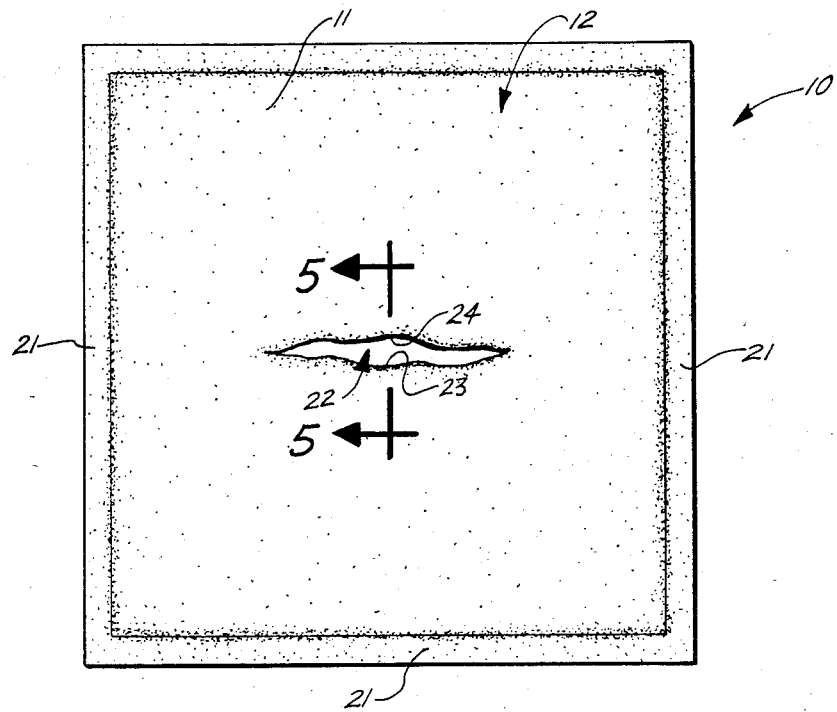
FIG. 4 is a top view of the preferred embodiment of the apparatus of the present invention.
Figure 5:
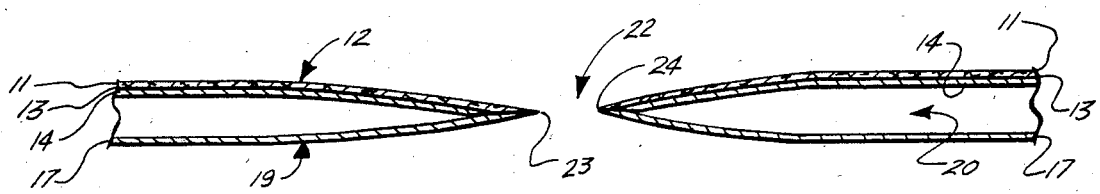
FIG. 5 is a sectional view taken along lines 5—5 of FIG. 4.

FIG. 4 schematically illustrates drape 10 as providing a central aperture 22. Aperture 22 provides a pair of edges 23, 24 which are joined at their end portions. Aperture 22 and more particularly edges 23, 24 would similarly provide a bound border similar to the peripheral edge 21 of FIG. 2. Thus, any apertures cut into or molded into drape 10 would be bound at the edges 23, 24 thereof using a layered, bound construction as shown in FIG. 2 of the drawings and designated at 21.

Figure 3:
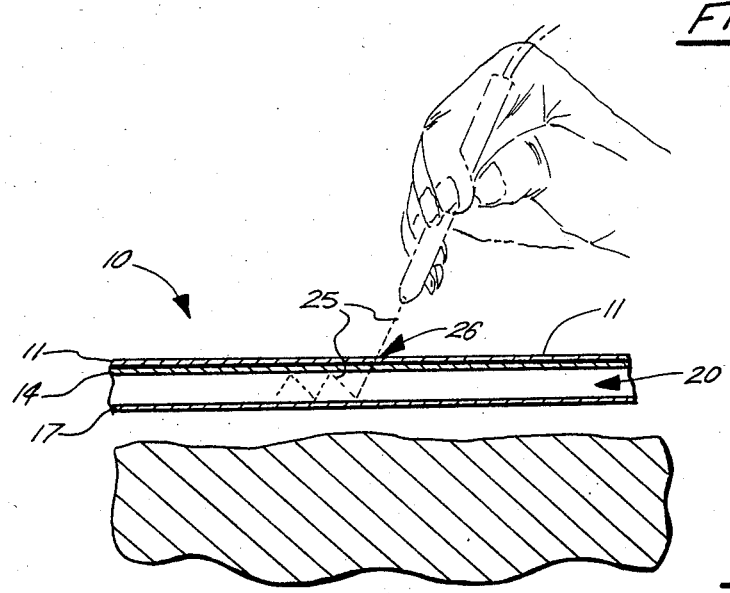
FIG. 3 is a schematic, sectional elevation of the preferred embodiment of the apparatus of the present invention shown during use.

The outermost layer 14 would preferably be a nonflammable fiber paper which could be as desired absorbent or repellant of water. The uppermost, non-metallic layer 11 would be bonded to upper metallic layer 14 which would preferably be a thin aluminum, highly reflective foil material which was blackened on its upper surface 15 and which was highly polished on its lower surface 16. The bonding substance 11 could be any glue type or like chemical product which can be sprayed or thermally pressed into the foil, metallic layer 14 and non-metallic layer 11. The construction as described provides an air space or "dead zone" which is surrounded by highly polished, reflective surfaces which could be, for example, highly polished aluminum foil. This construction allows the entry of a photon which is schematically illustrated by the dotted line 25 in FIG. 3, the point of entry being designated as 26 in the drawing. The photon enters at 26 through upper non-metallic layer 11 and upper metallic layer 14. The photon simply burns into the upper non-metallic layer 11 of paper or fabric set, for example, then through the bonding substance 13 which binds the layers 11, 14 together. Because the bonding material, such as glue causes a poor reflectance on the uppermost surface 15 of layer 14, the photon will further penetrate the layer 14 and enter the air space or dead area 20 creating a small hole. The laser energy will then be entrapped between the two highly reflective surfaces 16, 18. In so doing, the laser beam is entrapped and potential reflection into the room from other highly polished surfaces is prevented. The result is that the room and personnel associated with the surgical operation are protected from laser beams bouncing into their eyes. The patient is protected from having accidental laser beam exposure to skin areas should the laser be activated and not be properly pointed at the surgical operative area of the area as is desired.

Because many varying and different embodiments may be made within the scope of the inventive concept herein taught, and because many modifications may be made in the embodiments herein detailed in accordance with the descriptive requirement of the law, it is to be understood that the details herein taught are to be interpreted as illustrative and not in a limiting sense.

What is claimed as the invention is:

1. A laser surgery drape for use in protecting a patient from the radiation of a medical operating laser during surgery comprising:
    a. a multi-layered drape that can be draped upon the patient, having at least one metallic layer adhered to at least one non-metallic fabric-like layer; and
    b. reflective surface means positioned to reflect laser radiation toward the metallic and non-metallic layers for diffusing any laser radiation ray which is emitted from the medical operating laser and penetrates the metallic and non-metallic layers.

2. The laser surgery drape of claim 1, wherein the multi-layered drape comprises:
    a first non-metallic layer;
    a pair of metallic layers fastened to the non-metallic layer so that at least one of the metallic layers provides an inner surface which faces the inner surface of the other layers defining an air space therebetween;
    one of the metallic reflective surfaces adhered to the inner surface of the non-metallic layer.

3. The laser surgery drape of claim 1, wherein the layers are peripherally joined so that an air space is formed between the two layers, each layer having a laser metallic reflective surface which communicates with the air space.

4. The laser surgery drape of claim 3, wherein the reflective surfaces are flexible metallic surfaces.

5. The laser surgery drape of claim 4, wherein the flexible metallic surfaces are polished, mirrored surfaces.

6. The laser surgery drape of claim 1, wherein the non-metallic layer is a fabric.

7. The laser surgery drape of claim 1, wherein the non-metallic layer is paper.

8. The laser surgery drape of claim 1, wherein the metallic layer is aluminum.

9. The laser surgery drape of claim 1, wherein the multi-layered drape provides an aperture having aperture edges which are bonded together.

10. The laser surgery drape of claim 3, further comprising an aperture having edges which are peripherally joined so that an air space is formed between the two layers which terminates at the peripheral edge of the drape and at the edges of the aperture.

11. The method of protecting a patient during laser surgery from medical operating laser radiation by draping the patient's body with a laminated drape comprised of metallic and non-metallic layers including two layers which provide facing reflective surfaces with a space therebetween that can diffuse laser radiation entering the space.

12. The method of claim 11 wherein the drape of metallic and non-metallic layers respectively includes a metal foil layer and a fabric-like layer.

13. The method of claim 11 wherein the drape of metallic and non-metallic layers respectively includes a metal foil layer and a paper layer.

14. The method of claim 11 wherein the non-metallic layer is a cloth fabric layer.

15. The method of claim 11 wherein the non-metallic and metallic layers are bonded together.

16. The method of claim 11 wherein the medical laser is a medical carbon dioxide laser.

17. The method of claim 11 wherein the medical laser is a Nd:YAG type laser.

18. The method of claim 11 wherein the medical laser is an Argon laser.

* * * * *